(12) United States Patent
Jamil

(10) Patent No.: US 12,116,805 B2
(45) Date of Patent: Oct. 15, 2024

(54) DOOR HANDLE SANITIZER

(71) Applicant: Jimmy Jamil, Troy, MI (US)

(72) Inventor: Jimmy Jamil, Troy, MI (US)

( * ) Notice: Subject to any disclaimer, the term of this patent is extended or adjusted under 35 U.S.C. 154(b) by 627 days.

(21) Appl. No.: 17/363,594

(22) Filed: Jun. 30, 2021

(65) Prior Publication Data

US 2021/0404211 A1    Dec. 30, 2021

Related U.S. Application Data

(60) Provisional application No. 63/045,965, filed on Jun. 30, 2020.

(51) Int. Cl.
*E05B 1/00* (2006.01)
*A61L 2/10* (2006.01)
*A61L 2/24* (2006.01)

(52) U.S. Cl.
CPC .............. *E05B 1/0069* (2013.01); *A61L 2/10* (2013.01); *A61L 2/24* (2013.01); *A61L 2202/11* (2013.01); *A61L 2202/14* (2013.01)

(58) Field of Classification Search
CPC ................................. A61L 2/10; E05B 1/0069
See application file for complete search history.

(56) References Cited

U.S. PATENT DOCUMENTS

2021/0353786 A1\* 11/2021 Crosby ................. A61L 2/0047

FOREIGN PATENT DOCUMENTS

DE         102011001094 A1 \*  9/2012  ............... A61L 2/10

OTHER PUBLICATIONS

English Translation of Document No. DE 102011001094 A1 provided by the European Patent Office espacenet.com: Door Fitting For Door Assembly Used in E.g. Hospital; Sep. 6, 2012 (Year: 2012).\*

\* cited by examiner

*Primary Examiner* — Kevin Joyner

(57) ABSTRACT

The present invention provides a door handle enveloping sanitizer defined by a multi-apertured ring dimensioned to seat on or about a door handle be it either a round or elongated lever type which seats between a door and the grasping component of the door handle or knob. A plurality of UV emitting LED bulbs are housed in the ring and emit UV light which is beamed onto the grasping portion of the handle.

4 Claims, 5 Drawing Sheets

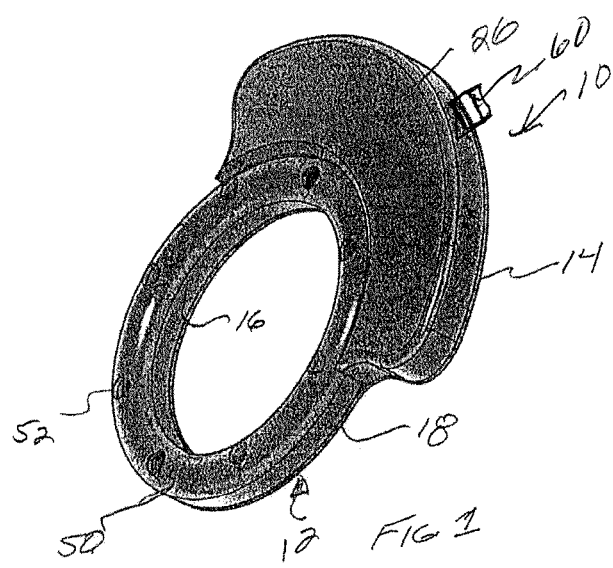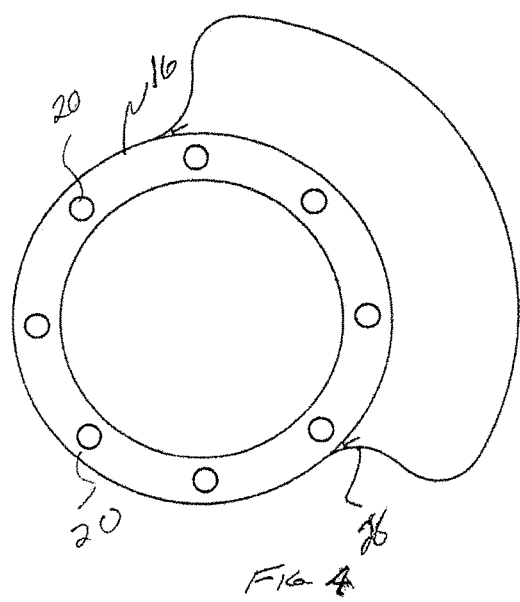

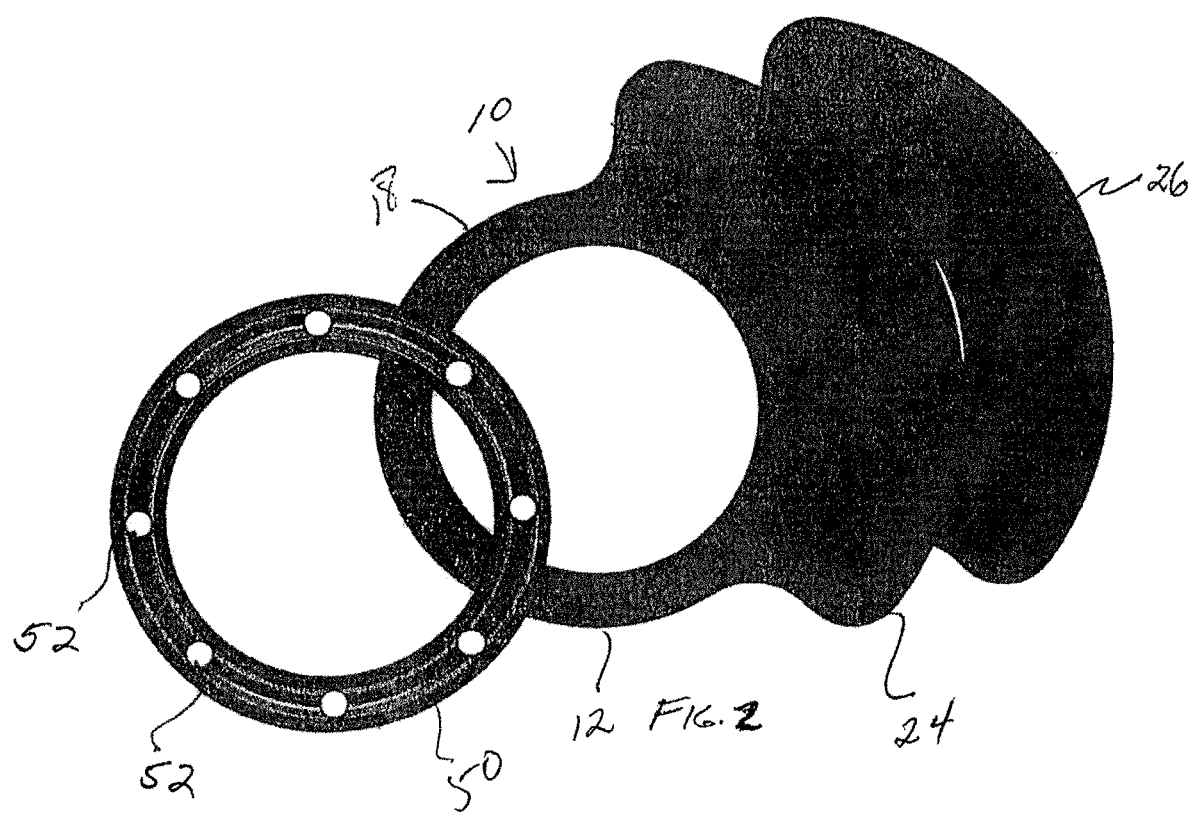

DOOR HANDLE SANITIZER

CROSS REFERENCE TO RELATED APPLICATIONS

This application is a completion application of U.S. Provisional Patent Application Ser. No. 63/045,965, filed Jun. 30, 2020 for "Door Handle Sanitizer", the entire disclosure of which is hereby incorporated by reference, including the drawing.

BACKGROUND OF THE INVENTION

1. Field of the Invention

The present invention concerns sterilizing or sanitizing devices. More particularly, the present invention concerns UV emitting sanitizing devices. Even more particularly, the present invention concerns door handle sanitizing devices.

2. Prior Art

In the present-day coronavirus environment, much attention has turned to sanitizing and/or sterilizing various surfaces. The pandemic created by the coronavirus has also spawned the creation of a multitude of means and methods for potentially protecting a person not only from exposure but from the prevention of contracting the coronavirus. Thus, people have turned to wearing masks, facial shields, gloves, as well as using hand gel sterilizing compositions, and so forth. Also, much attention has been addressed to the cleaning of surfaces such as table-tops, etc. Yet, one of the more commonly encountered devices on a daily basis, are doorknobs and door handles that persons use an innumerable amount of times on a daily basis. Thus, people have turned to weaving masks, facial shields, gloves, hand gel sterilizing compositions and so forth. Also, much attention has been addressed to the cleaning of surfaces such as table-tops, etc. Yet, one of the more commonly encountered devices on a daily basis, is a doorknob or door handle in which ungloved persons use innumerable amount of times. There exists a need for a device which can readily sanitize a door handle, especially on a continuing basis. It is to this to which the present invention is directed.

SUMMARY OF THE INVENTION

The present invention generally comprises a door enveloping handle sanitizer comprising a ring dimensioned to seat on or about a door handle be it either a round or elongated lever type and which seats between a door and the grasping component of the door handle or knob.

The ring is a multi-apertured device which emits UV light around and about the door facing portion of the handle itself.

A storage housing is integrally formed with the ring and is used to store a power source as well as an electronic device comprising a motion sensor and an accelerometer.

The power source, preferably, comprises rechargeable batteries such that the device is capable of sanitizing on a twenty-four-hour basis.

Optionally, a switch can be integrated into the electronic sanitizer off to prevent drainage of the battery.

A series of UV LED light bulbs are disposed within the ring which are in proximity to the apertures to enable UV light to radiate through the openings.

For a more complete understanding of the present invention reference is made to the following detailed description and accompanying drawing. In the drawing like reference characters refer to like parts throughout the several views in which:

BRIEF DESCRIPTION OF THE DRAWINGS

FIG. 1 is a perspective view of the door handle engaging sanitizer in accordance with the present invention;

FIG. 2 is an exploded, perspective view of the device hereof;

FIG. 4 is a top view of the top of the ring and housing;

DESCRIPTION OF THE INVENTION

Figure 3:
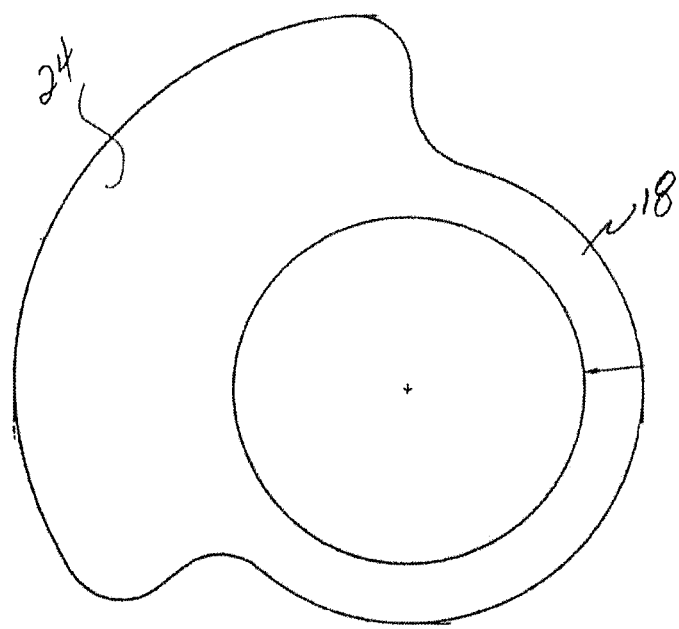
FIG. 3 is a plan view of the base of the ring and housing.
Figure 6:
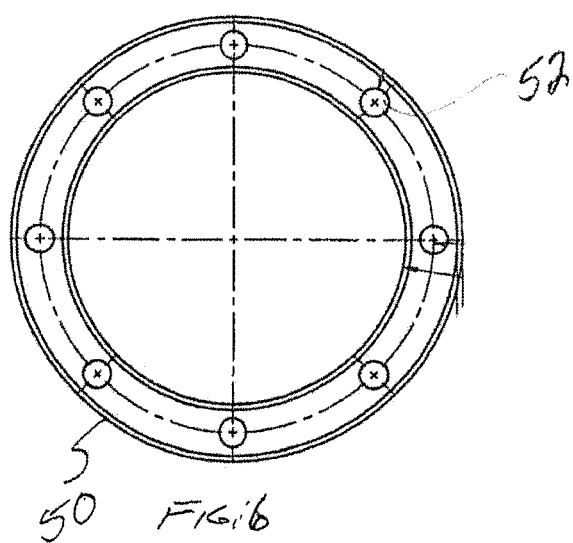
FIG. 6 is a top view of a clear protective shield.

Now, and with reference to the drawing, there is depicted therein a door handle sanitizer in accordance with the present invention and, generally, depicted at 10.

As shown, the device 10 includes an annular ring 12 and a housing 14.

The annular ring is preferably a three-part ring having a top piece or component 16, a sidewall 17, and a bottom ring or base 18, as detailed below which is integrally formed with the base portion 19 of the housing 14 and a clear cover 50.

The top piece or component or upper ring 16 is multi-apertured such as at 20.

The top piece 16 may be snap fitted to the base 18. The top piece 16 and base 18 cooperate to define a cavity in which is housed a plurality of LED UV emitting bulbs 22. The bulbs 22 are in registry with associated apertures 20 in the top ring.

As shown, the base and the top ring are fitted together by any suitable mode such as by snap fitting, gluing for permanent assembly or the like.

As described below, the LED bulbs 22 are wired in series such that they emit the UV light continuously and at the same power.

The housing 14 is an arcuate structure having a base 24, which as noted above, is integrally formed with the bottom or base 18. The housing includes a top 26 having a sidewall 27. Preferably, the base 24 and the top 26 are fitted together such as by snap fitting as at 28, gluing or the like.

The base 24 and top 26 cooperate to define a cavity 31 therebetween. The top 26 has the same curvature as the base 24 as well as comporting to the circumference of the ring 12.

As noted above, a controller, such as a pcBoard 40 is disposed in the housing cavity 31 and is in electrical communication, via lead wires, with the LED bulbs 22 in the well-known manner.

The pcBoard includes circuitry which comprises a motion detector sensor and an accelerometer which detects the opening and closing of a door.

A power source, such as batteries 30, are stowed in the housing cavity and powers the pcBoard to, in turn, actuate the bulbs 22.

Lead wires (not shown) extend from the pcBoard through the housing into the ring and to the LED bulbs. Alternatively, connectors may be used to interconnect the pcBoard to the bulbs.

Preferably, the UV lights are on continuously, but an externally operated power switch 60 may be interposed the batteries and the pcBoard to enable intermittent shutting off and/or turning on of the LED bulbs.

Figure 5:
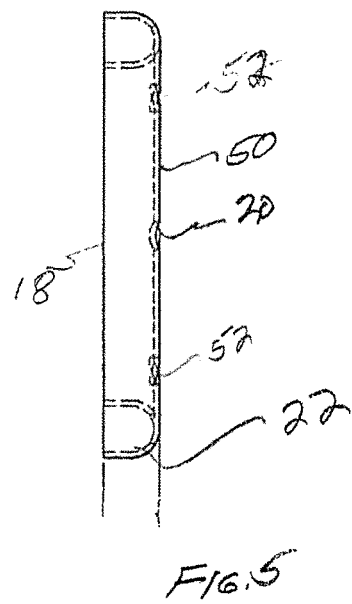
FIG. 5 is a side view of the ring, partly in phantom, showing the assembled ring and cover.
Figure 7:
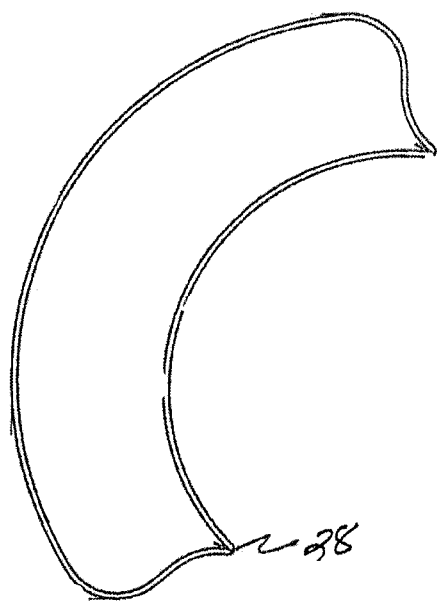
FIG. 7 is a top view of the housing.
Figure 8:
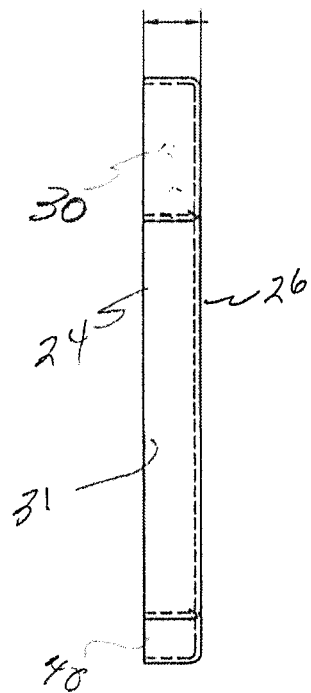
FIG. 8 is a side view of the ring.

Referring now to FIGS. 4 and 5, in order to protect the annular ring 12 from damage, a clear, hard, plastic cover 50 envelopes the ring. The cover is multi-apertured as at 52. The apertures 52 are in registry with the apertures 20 to enable the UVC light to emit therethrough. The cover 50 is snap fitted to the base 18.

In fabricating the present device, optimally, the ring and the base are from a synthetic resinous material such as PLA because of its biodegradability.

As noted, in use, the ring is mounted about the door handle, actuated by emplacing the battery(ies) in the housing into electrical communication with the pcBoard, which, in turn, powers the bulbs to continually emit UV light to maintain the door handle in a sanitary condition.

The invention claimed is:

1. A door handle sanitizer which comprises: a hollow annular ring comprising a bottom annular ring and a top annular ring which mates with the bottom ring to define a hollow interior therebetween, the top ring having a plurality of apertures circumferentially formed thereabout;

a plurality of UV light emitting bulbs disposed within the hollow interior of the annular ring and each one bulb in registry with an associated aperture formed in the top ring; and a housing attached to the bottom ring for storing a power source and a controller, the power source in electrical communication with the controller, the power source powers the bulbs.

2. The sanitizer of claim 1 wherein the controller comprises (a) a pcBoard defining the requisite circuitry for controlling the bulbs (b) a motion sensor and (c) an accelerometer;

the motion sensor and accelerometer detecting the opening and closing of a door and seated with the handle to control the light emitted by the bulbs.

3. The sanitizer of claim 1 which further comprises a plastic cover enveloping the top ring, the cover having a plurality of apertures which are in registry with the apertures formed in the top ring to enable the UV light to emit therethrough.

4. The sanitizer of claim 3 wherein the annular ring is a three-part ring having a top piece, sidewall and bottom ring, the bottom ring defining a base which is integrally formed with the housing and including the cover.

* * * * *